(12) United States Patent
Kuo et al.

(10) Patent No.: US 8,614,196 B2
(45) Date of Patent: Dec. 24, 2013

(54) **TREATMENT AND/OR PREVENTION OF INFLAMMATION AND CUTANEOUS PHOTODAMAGE AND PHOTOPROTECTION OF THE SKIN WITH A WATER-SOLUBLE EXTRACT FROM PLANT OF *SOLANUM* GENUS**

(75) Inventors: Kou-Wha Kuo, Kaohsiung (TW); Hamm-Ming Sheu, Kaohsiung (TW)

(73) Assignee: G & E Herbal Biotechnology Co., Ltd., Tainan (TW)

( * ) Notice: Subject to any disclaimer, the term of this patent is extended or adjusted under 35 U.S.C. 154(b) by 0 days.

(21) Appl. No.: 13/368,894

(22) Filed: Feb. 8, 2012

(65) Prior Publication Data

US 2012/0289473 A1 Nov. 15, 2012

(30) Foreign Application Priority Data

May 12, 2011 (TW) .............................. 100116659 A

(51) Int. Cl.
*A61K 31/706* (2006.01)
(52) U.S. Cl.
USPC .......................................................... 514/26
(58) Field of Classification Search
USPC .......................................................... 514/26
See application file for complete search history.

(56) References Cited

U.S. PATENT DOCUMENTS

| | | | |
|---|---|---|---|
| 6,699,486 | B1 | 3/2004 | Bolla |
| 7,078,063 | B2 | 7/2006 | Kuo |
| 2004/0247715 | A1 | 12/2004 | Kuo |
| 2012/0283202 | A1* | 11/2012 | Kuo et al. ....................... 514/26 |

FOREIGN PATENT DOCUMENTS

| | | |
|---|---|---|
| AU | 540812 | 11/1980 |
| CA | 1 151 549 | 8/1983 |
| CA | 2 489 675 | 1/2004 |
| CN | 1565473 | 1/2005 |
| CN | 101337000 | 1/2009 |
| CN | 101337001 | 1/2009 |
| CN | 101377475 | 3/2009 |
| EP | 0 020 029 | 12/1980 |
| EP | 1 508 334 A1 | 2/2005 |
| EP | 2522357 A1 | 11/2012 |
| JP | 2010-273593 | 12/2010 |
| RU | 2012107715 | 9/2013 |
| TW | I300352 | 9/2008 |
| WO | WO 00/61153 | 10/2000 |
| WO | WO 03/029269 | 4/2003 |
| WO | WO 03/ 030884 A2 | 4/2003 |
| WO | WO 03/030915 | 4/2003 |
| WO | WO 2004/002497 | 1/2004 |

OTHER PUBLICATIONS

Glossary of medical education terms, Institute of International Medical Education. http://www.iime.org/glossary.htm Accessed in Mar. 2013.*
Gilchrest BA. A review of skin ageing and its medical therapy. Br J Dermatol 135:867-875, 1996.*
Moynagh PN. TLR signalling and activation of IRFs: revisiting old friends from the NF-kB pathway. Trends Immunol 26:469-476, 2005.*
Glossary of Medical Education terms, Institute of International Medical Education.; (2) A Review of Skin Ageing and its Medical Therapy, B.A. Gilchrest, Br J Dermatol 135:867-875, 1996; and (3) TLR Signaling and Activation of IRFs: Revisiting Old Friends from the NF-kB Pathway, Paul N. Moynagh, Trends in Immunology vol. 26, No. 9, Sep. 2005. http://www.iime.org/glossary.htm.
Wu et al.; "*Solanum incanum* extract (DR-T100) induces human cutaneous squamous cell carcinoma apoptosis through modulating tumor necrosis factor receptor signaling pathway"; Journal of Dermatological Science 63 (2011) pp. 83-92.
Effects of *Solanum nigrum* L., 2013; http://mypaper.pchome.com.tw/tony168324/post/1321648323.
English-language translation of Office Action issued on Aug. 9, 2013, in Application No. RU2012107715 (7 pages).
Minina S.A., et al. "Chemistry and Technology of Phytopreparations," textbook the 2nd edition, Moscow: GEOTAR-Media Publishing Group (2009). (Citation D4, pp. 327 and 328).

* cited by examiner

*Primary Examiner* — Wu-Cheng Winston Shen
*Assistant Examiner* — Yih-Horng Shiao
(74) *Attorney, Agent, or Firm* — Pillsbury Winthrop Shaw Pittman LLP

(57) ABSTRACT

The present invention relates to a pharmaceutical composition for preventing and treating inflammation and cutaneous photodamage, which contains a water-soluble extract from a plant of *Solanum* genus. The composition also has a photoprotective effect, and can be used as a cosmetic composition.

15 Claims, 13 Drawing Sheets

Pathological control group | Experimental group 2

TREATMENT AND/OR PREVENTION OF INFLAMMATION AND CUTANEOUS PHOTODAMAGE AND PHOTOPROTECTION OF THE SKIN WITH A WATER-SOLUBLE EXTRACT FROM PLANT OF *SOLANUM* GENUS

CROSS-REFERENCE TO RELATED APPLICATION

This application claims priority of Taiwanese application no. 100116659, filed on May 12, 2011.

BACKGROUND OF THE INVENTION

1. Field of the Invention

The present invention relates to a pharmaceutical composition for preventing and treating inflammation and cutaneous photodamage, which contains a water-soluble extract from a plant of *Solanum* genus. The composition also has a photoprotective effect, and can be used as a cosmetic composition.

2. Description of the Related Art

In aerobic organisms, oxygen is utilized in aerobic respiration, thereby producing reactive oxygen species (ROS) and free radicals. Ultraviolet (UV), ionizing radiation, and certain medications or xenobiotics will also stimulate production of ROS and free radicals. ROS and free radicals are likely to react with components within the cell (e.g., DNA, protein and lipids etc.) due to instability thereof, thereby resulting in oxidative damage to cells and tissues.

In general, antioxidant enzymes in organisms form an interacting network to protect cells and tissues from oxidative damage. Oxidative stress forms when ROS and free radicals exceed the antioxidant capacity provided by the interacting network of the cells or tissues. It has been reported that oxidative stress plays an important role in the pathological process of inflammation and photodamage (Simon R. et al (2010), *Free radical biology & Medicine*, 49:1603-1616; Afaq F. et al. (2006), *Experimentla Dematology*, 15:678-684).

Inflammation is a protective response of cells or tissues to pathogen and external stressful stimuli. During inflammation, the cells or tissues at a site of injury will stimulate the expression of specific genes through NF-kB, followed by an increased expression of chemokines, thereby leading to the accumulation of polynuclear leukocytes, monocytes, macrophages and mast cells at the site of injury (i.e., infiltration). The recruited macrophages will be activated by lipopolysaccharides (LPS) that are expressed on a surface of a pathogen. The activated macrophages will induce the expression of proinflammatory genes (including cylooxygenase-2 gene, COX-2, and inducible nitric oxide synthase gene, iNOS) to reinforce inflammatory response. In addition, the activated macrophages release ROS and free radicals to kill pathogens. However, prolonged inflammatory response leads to oxidative stress and damage due to excess accumulation of ROS and free radicals, thereby resulting in chronic inflammation and ultimately potentiating the possibility of chronic illnesses or cancer.

Photodamage occurs when skin of an organism is exposed to ultraviolet (especially ultraviolet-B, UV-B), leading to skin damage. Exposure to UV radiation will accelerate the accumulation of ROS and free radicals in skin cells, increase oxidative stress to the skin cells and induce expression of matrix metalloproteinases (MMP), thereby resulting in oxidative photodamage. Symptoms of oxidative photodamage include: telangiectasia, thinning of epidermis, reduction in collagen fiber and elastic fiber, dryness, wrinkle formation, inflammatory cell infiltration, premature skin aging and skin pathologic change.

In recent years, phytochemicals or phytochemopreventive agents derived from plants have been proven to have antioxidant, anti-inflammatory properties and improve photodamage. Examples of the phytochemical include: green tea polyphenols (GTPs), epigallocatechin gallate (EGCG), genistein, resveratrol, curcumin, apigenin, lycopene, etc. (Adhami V. M. et al (2008), *Photochem. Photobiol.*, 84:489-500). The phytochemicals have been proven to be safer for clinical application without undesired side effects, and have caught attention in the field of medical research.

Plants of *Solanum* genus include *Solanum incanum* L., synonymous with *Solanum undatum*, *Solanum incanum* Ruiz. & Pav., *Solanum coagulans* Forsskal; bitter apple in English), *Solanum indicum*, *Solanum nigrum* (Long kui in Chinese; black nightshade in English), *Solanum capsicastrum* (false jerusalem cherry in English), *Solanum xanthocarpum*, *Solanum melongena*, *Solanum coagulans*, *Solanum tuberosum*, *Solanum sodomeum* (apple of Sodom in Australia), *Solanum turburosum*, *Solanum aculeastrum*, *Solanum lycocarpum*, *Solanum khasianum*, *Solanum suaveolens*, *Solanum uporo*, *Solanum abutiloides*, *Solanum coccineum*, *Solanum unguiculatum*, *Solanum robustum*, *Solanum anguivi*, *Solanum platanifolium*, *Solanum mammosum*, etc. It is known that steroidal alkaloids can be extracted from the *Solanum* genus, and commonly include solasonine and solamargine.

U.S. Pat. No. 7,078,063 B2 issued to the inventors of the present invention discloses a water-soluble extract from a plant of *Solanum* genus, especially *Solanum incanum* L., which includes at least 60 wt % of solasonine and solamargine., and a method for preparing the water-soluble extract. The patent is hereby incorporated by reference in its entirety.

In the aforesaid US patent, the inventors found that the water-soluble extract can inhibit the growth of tumor/cancer cells (specifically liver tumor cells, lung cancer cells, and breast cancer cells). In this invention, the inventors unexpectedly found that the water-soluble extract effectively cure and/or prevent inflammation and cutaneous photodamage.

SUMMARY OF THE INVENTION

Therefore, according to the first aspect, this invention provides a pharmaceutical composition for preventing and treating cutaneous photodamage, comprising a water-soluble extract from a plant of *Solanum* genus, the water-soluble extract comprising solamargine and solasonine.

In the second aspect, this invention provides a method for preventing and treating cutaneous photodamage, comprising applying to a subject in need of such treatment a water-soluble extract from a plant of *Solanum* genus, the water-soluble extract comprising solamargine and solasonine.

In the third aspect, this invention relates to the use of a water-soluble extract from a plant of *Solanum* genus in the manufacture of a medicament for preventing and treating cutaneous photodamage, the water-soluble extract comprising solamargine and solasonine.

In the fourth aspect, this invention provides a cosmetic composition, comprising a water-soluble extract from a plant of *Solanum* genus, the water-soluble extract comprising solamargine and solasonine.

In the fifth aspect, this invention provides a pharmaceutical composition for preventing and treating inflammation, comprising a water-soluble extract from a plant of *Solanum* genus, said water-soluble extract comprising solamargine and solasonine.

In the sixth aspect, this invention provides a method for preventing and treating inflammation, comprising applying to a subject in need of such treatment a water-soluble extract from a plant of *Solanum* genus, the water-soluble extract comprising solamargine and solasonine.

In the seventh aspect, this invention relates to the use of a water-soluble extract from a plant of *Solanum* genus in the manufacture of a medicament for preventing and treating inflammation, the water-soluble extract comprising solamargine and solasonine.

BRIEF DESCRIPTION OF THE DRAWINGS

Other features and advantages of the present invention will become apparent in the following detailed description of the preferred embodiments of the invention, with reference to the accompanying drawings in which.

DETAILED DESCRIPTION OF THE PREFERRED EMBODIMENTS

Figure 1:
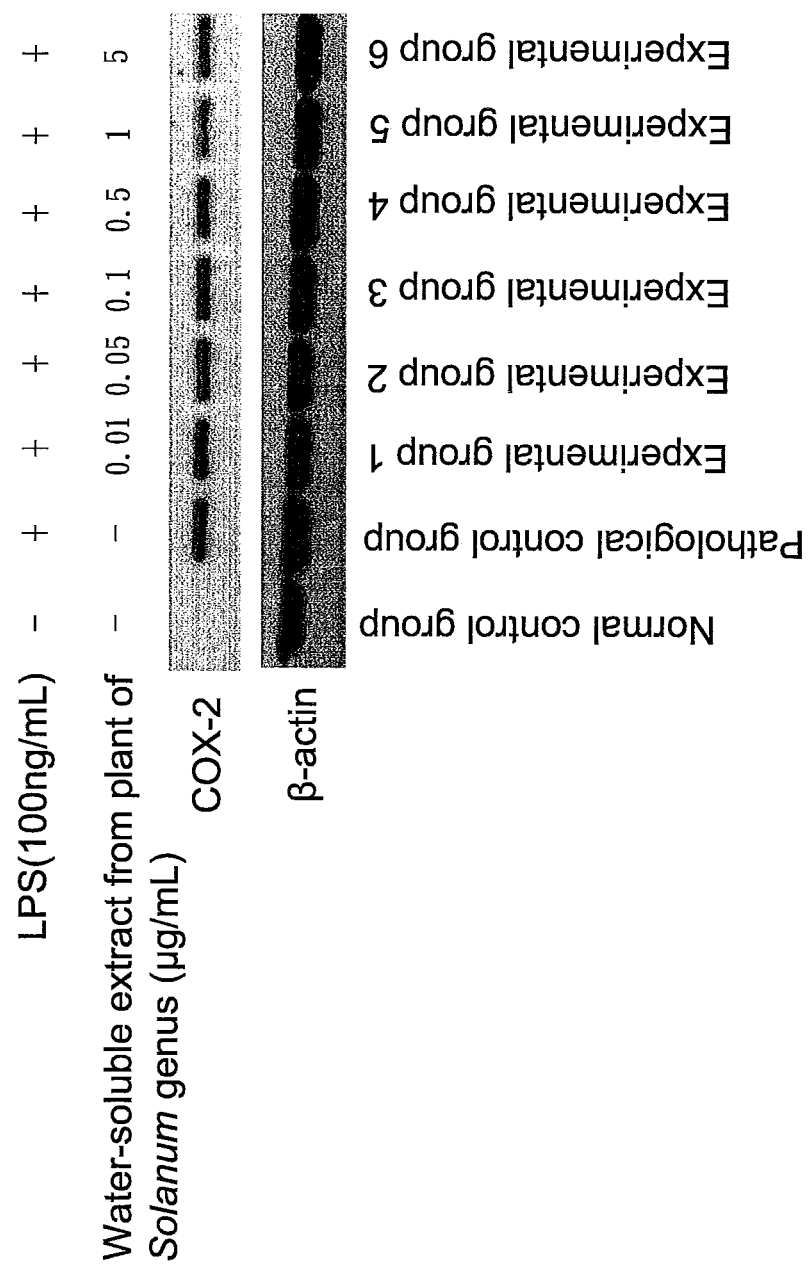
FIG. 1 is a western blot, showing COX-2 expression in RAW264.7 cell after LPS-induced inflammatory response. The cells in normal control group were not treated with LPS and a water-soluble extract from a plant of *Solanum* genus, whereas cells in pathological control group were treated with 100 ng/mL of LPS. Experimental groups 1-6 were treated with various concentrations of the water-soluble extract (0.01, 0.05, 0.1, 0.5, 1 and 5 µg/mL) along with 100 ng/mL of LPS.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the words "comprises," "contain" and variants thereof have a corresponding meaning.

Unless otherwise defined, all technical and scientific terms used herein have the meaning commonly understood by a person skilled in the art to which this invention belongs. One skilled in the art will recognize many methods and materials similar or equivalent to those described herein, which could be used in the practice of this invention. Indeed, this invention is in no way limited to the methods and materials described. For clarity, the following definitions are used herein.

The present invention provides a pharmaceutical composition for preventing and treating inflammation, which includes a water-soluble extract from a plant of *Solanum* genus. The water-soluble extract comprises solamargine and solasonine. Preferably, the water-soluble extract comprises at least 60 wt % solamargine and solasonine, more preferably, 60 wt %-90 wt % of solamargine and solasonine.

A process for preparing the water-soluble extract has been disclosed in U.S. Pat. No. 7,078,063 B2, and includes the following steps:

(a) subjecting a plant material of a plant of *Solanum* genus to an extraction treatment using an acidic aqueous solution with a pH value of 3-5, such that an aqueous solution is obtained;

(b) adjusting the pH value of the aqueous solution obtained in step (a) to pH 8-10 with a base, such that a precipitate is formed;

(c) washing the precipitate formed in step (b) with water, followed by drying, such that a dried product is obtained;

(d) admixing the dried product obtained in step (c) with chloroform, followed by addition of a suitable amount of a 100% alcohol, such that a chloroform-alcohol mixture is formed;

(e) mixing the chloroform-alcohol formed in step (d) with a water/alcohol solution having a predetermined water/alcohol ratio, such that a mixture containing a chloroform-based layer and a non-chloroform-based layer is obtained;

(f) removing the chloroform-based layer from the mixture obtained in step (e), followed by addition of a suitable amount of water; and (g) obtaining a supernatant from the resultant mixture of step (f), followed by drying the supernatant, wherein the resultant dried product is able to be directly dissolved in water to form a yellowish clear and transparent aqueous solution.

Preferably, the water-soluble extract of a plant of *Solanum* genus has been obtained at least from the fruit, root, stem and leaf of the plant of *Solanum* genus. The plant of *Solanum* genus has been chopped in a preliminary treatment. In a preferred embodiment of this invention, the plant material used in step (a) is the fruit of the plant of *Solanum* genus.

The inventors found that certain factors might affect the content and proportion of solasonine and solamargine in the water-soluble extract obtained using the aforesaid process. These factors include the species of the plant of *Solanum* genus and the part(s) of the plant used in the extracting process, as well as the types of alcohol and base used. Therefore, a skilled artisan can prepare a desired water-soluble extract by selecting suitable species of the plant, in conjunction with appropriate operating conditions.

Preferably, the water-soluble extract is obtained from a plant of *Solanum* genus selected from the group consisting of *Solanum ihcanum* L., *Solanum indicum*, *Solanum nigrum*, *Solanum capsicastrum*, *Solanum xanthocarpum*, *Solanum melongena*, *Solanum coagulans*, *Solanum tunigrum*, *Solanum sodomeum*, *Solanum turburosum*, *Solanum aculeastrum*, *Solanum lycocarpum*, *Solanum khasianum*, *Solanum suaveolens*, *Solanum uporo*, *Solanum abutiloides*, *Solanum coccineum*, *Solanum unguiculatum*, *Solanum robustum*, *Solanum anguivi*, *Solanum platanifolium* and *Solanum mammosum*. In a preferred embodiment of this invention, the water-soluble extract is obtained from *Solanum incanum* L.

In preliminary experiments, in vitro data have shown that the water-soluble extract from *Solanum* genus can inhibit inflammatory response induced by LPS. It has also been proven that, after hairless mice with UV-B induced inflammation are treated with the water-soluble extract from *Solanum* genus, the expression of NF-kB, COX-2 and iNOS on skin tissue thereof was markedly decreased, together with an alleviation of mast cell infiltration and inflammatory response.

Therefore, this invention provides a method for preventing and treating inflammation, comprising applying to a subject in need of such treatment the water-soluble extract or the pharmaceutical composition.

The administration route of the aforesaid pharmaceutical composition provided by this invention comprises, but is not limited to oral, topical and parenteral routes.

The pharmaceutical composition provided by this invention can be formulated into an oral dosage form using technology well known to a skilled artisan. Examples of the oral dosage form include, but are not limited to: aseptic power, tablet, troche, lozenge, pellet, capsule, dispersible powder or granule, solution, suspension, emulsion, syrup, elixir, slurry, etc.

The pharmaceutical composition of this invention can further include a pharmaceutically acceptable carrier that is widely employed in drug-manufacturing technology.

The pharmaceutically acceptable carrier comprises one or more reagents, including: solvent, buffer, emulsifier, suspending agent, decomposer, disintegrating agent, dispersing agent, binding agent, excipient, stabilizing agent, chelating agent, preservative, wetting agent, lubricant, diluent, absorption delaying agent, liposome, sweetening agent, flavoring agent, coloring agent, etc. The choice and amount of the pharmaceutically acceptable carrier are within the expertise of those skilled in the art.

The pharmaceutically acceptable carrier comprises one or more reagents including, for example, water, normal saline, phosphate buffered saline (PBS), glucose containing solution, aqueous solution containing alcohol (for example, ethanol, propanediol, glycol, mannitol, etc.), oil (for example, peanut oil, olive oil, sesame oil, castor oil, cottonseed oil, soybean oil, etc.), glycerol, organic solvent and liposome. In an embodiment of this invention, the solvent is water.

The pharmaceutical composition according to this invention can be formulated into a suitable dosage form for topical administration using technology well known to those skilled in the art, which includes, but is not limited to, external preparations, effervescent tablets, suppositories, and the like.

In a preferred embodiment of this invention, the pharmaceutical composition of this invention is formulated into an external preparation in a gel form by admixing the water-soluble extract with a base that is well known and commonly used in the art.

In this invention, the suitable base may include one or more of the following additives: water, alcohols, glycol, hydrocarbons (such as petroleum jelly and white petrolatum), waxes (such as paraffin and yellow wax), preserving agents, antioxidants, surfactants, absorption enhancers, stabilizing agents, gelling agents (such as Carbopol®974P, microcrystalline cellulose and carboxymethylcellulose), active agents, humectants, odor absorbers, fragrances, pH adjusting agents, chelating agents, emulsifiers, occlusive agents, emollients, thickeners, solubilizing agents, penetration enhancers, anti-irritants, colorants and propellants etc. The choice and amount of these additives are within the expertise of those skilled in the art.

The dosage and frequency of administration of this pharmaceutical composition may vary depending on the following factors: the severity of the disease to be treated, the route of administration, and the weight, age, physical condition and response of the subject to be treated. For instance, the daily dosage of the pharmaceutical composition for topical administration according to this invention may be 10-20 mg/cm$^2$ of the lesion area and one to six times per day. The dosage of this pharmaceutical composition for oral administration may be 1-30 mg/Kg, 1-4 times a day.

The water-soluble extract from the plant of *Solanum* genus has been proven to alleviate skin pathological change induced by UV-B-induced cutaneous photodamage on hairless mice. In addition, it can effectively improve skin elasticity and solar elastosis, while maintaining moisture-retaining capacity at the same time.

Therefore, the present invention provides a pharmaceutical composition for treating and/or preventing cutaneous photodamage, which comprises the water-soluble extract from a plant of *Solanum* genus as described above. The present invention also provides a method for preventing and treating cutaneous photodamage, comprising applying to a subject in need of such treatment the aforesaid water-soluble extract or the pharmaceutical composition.

In this invention, the term "cutaneous photodamage" indicates skin damage caused by exposure of skin to sunlight or UV light (especially, UV-B). The cutaneous photodamage comprises, but is not limited to: thinning of the skin, skin atrophy, decrease in collagen fiber and elastic fiber, elastosis, loss of skin elasticity, dryness, wrinkle formation, inflammatory cell infiltration, premature skin aging, vascular change (such as diffuse erythema, ecchymosis, or telangiectasia), pigmentary change (such as lentigines, freckles, hypopigmentation or hyperpigmentation), comedone, cyst and skin pathological change.

According to this invention, the administration route, dosage and pharmaceutically acceptable carrier are similar to those used in the pharmaceutical composition for preventing and treating inflammation. In a preferred embodiment of the current invention, the pharmaceutical composition is formulated into topical form for administration onto the skin.

Due to prevention/protection of cutaneous photodamage of the water-soluble extract, one can predict that the water-soluble extract can be used as a cosmetic component to prepare a cosmetic composition.

Therefore, this invention provides a cosmetic composition with photoprotective effect, which comprises the water-soluble extract as described above.

In this invention, the term "photoprotective" indicates to block or alleviate adverse clinical, histological and immunological effects caused by the sun or ultraviolet. These effects include acute reactions (such as erythema and inflammation) and chronic effects (such as elastosis and wrikinle formation).

According to this invention, the cosmetic compositions further comprise cosmetically acceptable adjuvant that is widely employed in cosmetic-manufacturing technology.

The acceptable adjuvant comprises one or more reagents including solvent, gelling agent, activating agents, preservatives, antioxidants, screening agent, chelating agent, surfactants, coloring agent, thickening agent, filler, fragrance and odor absorbent. The choice and amount of these additives are within the expertise of those skilled in the art.

The cosmetic composition provided by this invention can be prepared using technology well known to a skilled artisan into the form of skincare, haircare or makeup products. The form includes, but is not limited to, aqueous solution, emulsion, gel, ointment, cream, mask, patch, powder, aerosol, spray, lotion, sunblock and other body cleansing products.

The cosmetic composition of this invention can be used with the following agents: whitening agents, humectants, bactericides, ultraviolet absorbers, anti-acne agent, antipruritic, antihyperkeratolytic agents, antipsoriatic agents, anti-ager, antiwrinkle agents, antiseborrheic agents, self-tanning agents and wound-healing agents. The choice and amount of these agents are within the expertise of those skilled in the art.

EXAMPLES

Experimental Materials

1. Preparations of Water-soluble Extract from *Solanum incanum* L. and *Solanum incanum* L. Solution Containing the Water-soluble Extract:

The water-soluble extract from *Solanum incanum* L. was prepared based on the procedure disclosed in Example 1 of U.S. Pat. No. 7,078,063 B2. Specifically, 500 g of ripe fruit of *Solanum incanum* L. was ground subsequent to addition of 1000 ml pure water. To the resultant aqueous mixture, 99.5% of acetic acid was added dropwise to adjust the pH value to 4.0, followed by shaking at room temperature for 12 hrs. A supernatant was obtained by centrifuging the aqueous mixture, and 33% $NH_4OH$ basic solution was added thereto dropwise to adjust the pH value of the supernatant to 9.0, and a precipitate was formed. The precipitate was obtained by conducting centrifugation at 4,500 rpm (Beckman Coulter, Avanti J-25, JA-14 Rotor), and the residual basic solution present therein was removed by washing the precipitate with water, followed by centrifugation at 4,500 rpm. The precipitate thus obtained was suspended in distilled water and subjected to lyophilization (Virtis, Freezemobile 12ES) to get 5 g of dried powder.

2 g of the dried powder was dissolved in 50 ml chloroform in reagent grade, followed by addition of 40 ml of 100% methanol and was shaken to form a uniform suspension. A supernatant was obtained by centrifugation at 4,500 rpm or filtration. 70 ml of methanol:water solution (1:1) was added to the supernatant and mixed well. The mixture obtained was centrifuged at 12,000 rpm for 10 min. The resultant supernatant was taken out, and 120 ml distilled water was added thereto and shaken well. Meanwhile, the supernatant became murky. The supernatant was further centrifuged at 12,000 rpm for 10 min so as to remove the precipitate. The resultant supernatant was subjected to decompress concentrating under reduced pressure at 55° C. to remove methanol, followed by lyophilization to obtain dried powder of the water-soluble extract.

The water-soluble extract was dissolved in sterilized water to obtain a *Solanum incanum* L. solution for further use in experiments described below.

2. Preparation of *Solanum incanum* L. Gel Containing the Water-soluble Extract:

4 g of Carbopol®974P, which was used as a gelling agent and is commercially available from Lubrizol Advanced Materials, Inc., KY 40258, USA, was dissolved in 50 g pure water, followed by sequentially adding 30 g propylene glycol and 7 g of the dried powder of the water-soluble extract obtained from the section of "1. Preparations of water-soluble extract from *Solanum incanum* L. and *Solanum incanum* L. solution containing the water-soluble extract" under "Experimental Materials" and mixing well. The mixture was heated in a heating vessel at a temperature of 50° C.-60° C. for 20 minutes, followed by cooling at room temperature. The cooled mixture was added with trienthanolamine to adjust pH to 7.0±0.5. Subsequently, water was added until the total weight of the mixture reached 100 g, thereby obtaining a gel containing 7% (w/w) of the water-soluble extract (hereinafter referred to as *Solanum incanum* L. gel).

3. Animal Model

HRS/J hairless mice (6-8 weeks old, body weight 20-22 g) were purchased from Jackson Laboratory (Bar Harbor, USA). The mice were kept in a room with 12 hr/12 hr light/dark cycle, temperatures of 21-22° C., and 30-70% humidity. Diet and water were sufficient and accessible to the mice at all times. All animal experiments were conducted according to Guide for the Care and Use of Laboratory Animals of National Institute of Health (NIH).

General Methods:

1. Analysis of Protein Products:

Sodium dodecyl sulfate-polyacrylamide gel electrophoresis (SDS-PAGE) and western blot were used for protein analysis in this invention. Apparatus and reagents for SDS-PAGE and western blot are as follows:

a. Vertical electrophoresis system (Hoefer SE600, GE Healthcare) were used for SDS-PAGE analysis.
b. Polyvinylidene difluoride membrane (PVDF, Millipore) and semi-dry blotters (Hoefer TE70X, GE Healthcare) were used for protein transfer.
c. Primary and secondary antibodies used in western blot method are listed in Table 1.
d. Proteins were visualized by chemiluminescence staining using Immobilon™ Western Chemiluminescent HRP Substrate (Millipore, Cat No. WBKLS0500), followed by detection on autoradiography films (Kodak Biomax, Kodak Cat. No. 1788207).

TABLE 1

Primary and secondary antibodies used in western blot analysis

| Target protein | Primary antibody | Secondary antibody |
|---|---|---|
| COX-2 | Mouse anti COX-2 monoclonal antibody (BD Bioscience, Cat. No. 610203) | Sheep anti mouse IgG-horseradish peroxidase (HRP) antibody (Amersham, Cat. No. NA931) |
| NF-κB | Rabbit anti NF-κB monoclonal antibody (Abcam, Cat. No. Ab7970) | Donkey anti rabbit IgG-HRP antibody (Amersham, Cat. No. NA934) |
| iNOS | Rabbit anti iNOS polyclonal antibody (Santa Cruz, Cat. No. Sc-651) | Donkey anti rabbit IgG-HRP antibody |
| β-actin | Mouse anti β-actin monoclonal antibody (Sigma, Cat. No. A5441) | Sheep anti mouse IgG-HRP antibody |
| GAPDH | Mouse anti GAPDH monoclonal antibody (Chemicon, Cat. No. Mab374) | Sheep anti mouse IgG-HRP antibody |

2. Induction of Inflammation and Photodamage:

Dorsal skin of each of the HRS/J mice was exposed to UV-B radiation three times a week for 14 weeks to induce inflammatory response and photodamage. The UVB radiation was carried out using BLX-312 ultraviolet crosslinker (BIO-LINK, Vilber Lourmat, France), which is equipped with 6×8W T-8M UV-B lamp (312 nm). The single dosage of UV-B radiation for each exposure, the UV-B dosage for one week (dosage/wk), and the cumulative dosage are listed in Table 2.

TABLE 2

| Experimental time point (wk) | Single UV-B dosage ($mJ/cm^2$) | Dosage/wk ($mJ/cm^2$) | Accumulated dosage ($mJ/cm^2$) |
|---|---|---|---|
| 1 | 36 | 108 | 108 |
| 2 | 54 | 162 | 270 |
| 3 | 72 | 216 | 486 |
| 4 | 90 | 270 | 765 |
| 5 | 108 | 324 | 1080 |
| 6 | 126 | 378 | 1458 |
| 7 | 144 | 432 | 1890 |
| 8 | 162 | 486 | 2376 |
| 9 | 180 | 540 | 2916 |

TABLE 2-continued

| Experimental time point (wk) | Single UV-B dosage (mJ/cm$^2$) | Dosage/wk (mJ/cm$^2$) | Accumulated dosage (mJ/cm$^2$) |
| --- | --- | --- | --- |
| 10 | 216 | 594 | 3510 |
| 11 | 216 | 648 | 4158 |
| 12 | 216 | 648 | 4806 |
| 13 | 216 | 648 | 5454 |
| 14 | 216 | 648 | 6102 |

3. Tissue Slice:

Tissues (harvested at room temperature) were fixed in 4% paraforaldehyde in PBS for at least 12 hrs, followed by ethanol dehydration. The dehydrated tissues were embedded in paraffin and sliced to obtain longitudinal sections.

4. Statistical Analysis:

Results are shown as mean±standard error mean (SEM). All statistical data analyses were performed by Student's t-test (2-tailed). P<0.05 is considered statistically significant.

Example 1

Evaluation of In Vitro Anti-inflammatory Effect of the Water-soluble Extract from *Solanum incanum* L Murine macrophage cell line RAW264.7 that was subjected to lipopolysaccharides (LPS)-induced inflammation was used to determine the anti-inflammatory effect of the water-soluble extract from *Solanum incanum* L.

Experimental Procedures:

RAW264.7 cells (purchased from American Type Culture Collection, ATCC, TIB-71) were seeded at a density of 1×10$^6$ cells/well (6-well plate) in Dulbecco's Modified Eagle's Medium (DMEM) (HyClone SH 30022.01, Logan, Utah, USA) with 10% fetal bovine serum (FBS), 4 mM L-glutamine and 4.5 g/L glucose (without sodium pyruvate), and incubated in a 37° C., 5% CO$_2$ incubator. The cells were divided into three groups: normal control group, pathological control group and experimental groups (experimental groups 1, 2, 3, 4, 5 and 6). After 72 hrs of incubation, the pathological control group was changed to be incubated in fresh DMEM medium containing 100 ng/mL of LPS (*Escherichia coli* serotype 0111:B4, Sigma), and the experimental groups were incubated in fresh DMEM media containing 100 ng/mL of LPS and different concentrations of the water-soluble extracts obtained from the section of "1. Preparations of water-soluble extract from *Solanum incanum* L. and *Solanum incanum* L. solution containing the water-soluble extract" under "Experimental Materials". The concentrations of the water-soluble extracts for experimental groups 1, 2, 3, 4, 5 and 6 were respectively 0.01, 0.05, 0.1, 0.5, 1 and 5 μg/mL. The normal control group was still incubated in DMEM with 10% FBS, 4 mM L-glutamine and 4.5 g/L glucose (without sodium pyruvate).

After 24 hrs of incubation (in a 37° C., 5% CO$_2$ incubator), the medium in each well was removed followed by addition of 100 μL T-PER reagent (purchased from PIERCE) and mixing to obtain a cell mixture. The cell mixture was placed in a centrifugation tube and shaken for 5 min followed by cooling on ice for 30 min. Subsequently, the cell mixture was centrifuged at 14,000 rpm for 10 min at 4° C. and a supernatant was collected as a protein sample for further analyses.

The resultant protein sample was subjected to COX-2 western blot analysis using the method described in the section of "1. Analysis of protein products" under "General Methods". β-actin was used as an internal control.

Results:

FIG. 1 is a western blot showing COX-2 expression in RAW264.7 cells. As shown in FIG. 1, COX-2 expression was markedly increased in the pathological control group when compared to the normal control group, which indicates a successful induction of inflammation by LPS in RAW264.7 cells. A decreased expression of COX-2 was observed in experimental group 1-6 when compared to the pathological control group, and the decreased expression is more obvious when a higher concentration of water-soluble extract was added. These data demonstrate that the water-soluble extract from *Solanum incanum* L. can inhibit LPS-induced inflammation in vitro, and the effect of the water-soluble extract on anti-inflammatory response is dose-dependent.

Example 2

Evaluation of the Therapeutic Effects of the *Solanum incanum* L. Solution and the *Solanum incanum* L. Gel on Hairless Mice with UV-B-induced Inflammation Experimental Procedures:

HRS/J hairless mice was randomly grouped into normal control group, pathological control group and two experimental groups (i.e. experimental group 1 and 2) (n=4/group). HRS/J hairless mice in normal control group did not receive any UV-B radiation. The mice in pathological control group and two experimental groups were induced inflammation using the procedure as described in the section of "2. Induction of inflammation and photodamage" under "General Methods".

Starting from the initiation of UVB radiation, HRS/J mice in experimental group 1 was administered orally with *Solanum incanum* L. solution, in which the solution was prepared as described in the section of "1. Preparations of water-soluble extract from *Solanum incanum* L. and *Solanum incanum* L. solution containing the water-soluble extract" under "Experimental Materials". These mice were administered with *Solanum incanum* L. solution once a day (1500 mg/kg), 7 times a week, during a 14-week (wk) period, and were continuously observed for 60 wks (i.e., 60 wk experimental period). On the UV-B exposed dorsal skin of each of the HRS/J hairless mice in experimental group 2, the *Solanum incanum* L. gel obtained from the section of "2. Preparation of *Solanum incanum* L. gel containing the water-soluble extract" under "Experimental Materials" was applied. The gel was applied once a day (dosage: 10-20 mg of gel per cm2), 5 times a week, during a 14-wk period and was observed for 60 wks. HRS/J hairless mice in normal control and pathological control group were not treated with the *Solanum incanum* L. solution nor the *Solanum incanum* L. gel.

After 6 wks of UVB radiation, HRS-J hairless mice were analyzed for Items A and B listed below. In addition, dorsal skin tissues were collected using surgical scissors from the mice in normal control group, pathological control group and experimental group 2 after the 60 wk experimental period. These tissues were analyzed for Items C to E listed below.

A. Diagnosis of Clinical Signs:

HRS/J hairless mice were observed for any signs of inflammation, e.g., itching, redness, etc. after 6 wks of UV-B radiation.

B. Analysis of Transepidermal Water Loss (TEWL)

After 6 wks of UV-B radiation, TEWL was evaluated on dorsal skin of each HRS/J hairless mouse from each group using an evaporimeter (Tewameter TM 201R, Courage & Khazaka, Cologne, Germany).

C. Western Blot Analysis of NF-κB, COX-2 and iNOS 0.5 g of skin tissue was added to T-PER tissue protein extraction reagent (Thermo Scientific, Cat. No. 78510), followed by tissue disruption by a homogenizer (purchased from Biospec Products). The well homogenized product was centrifuged at 15,000 rpm and 4° C. for 10 hrs. Supernatant was collected for protein analysis.

The isolated protein was further used to detect NF-κB, COX-2 and iNOS by western blot analysis according to the procedure set forth in the section of "1. Analysis of protein products" under "General Methods". GAPDH was used as an internal control.

D. Immunohistochemistry Stain of NF-κB

The skin tissues were sectioned into 6 μm thickness using the procedure set forth in the section of "3. Tissue slice" under "General Methods". The tissue sections were subjected to immunohistochemistry stain using primary antibody rabbit anti NF-κB monoclonal antibody and donkey anti rabbit IgG antibody conjugated with biotin (DarkoCytomation). The stained tissues were examined under an optical microscope (Olympus BX51, Japan) under 100 to 400× magnification, and was photographed using a digital camera (Olympus DP50, Japan).

E. Histochemistry Stain of Mast Cells

The skin tissues were sectioned into 6 μm thickness using the procedure set forth in the section of "3. Tissue slice" under "General Methods". The tissue sections were subjected to histochemistry stain with toluidine blue (Sigma, Cat No. T3260). The stained tissue sections were examined under an optical microscope with 100 to 400× magnification, and were photographed with a digital camera (Olympus DP50, Japan). Quantification of mast cell number was conducted by randomly selecting 5 tissue sections, and counting randomly 10 observing fields in each of the tissue sections. Data are shown as mean±SEM ($p<0.05$ is statistically significant).

Results:

A. Diagnosis of Clinical Signs

HRS/J hairless mice in pathological control group showed symptoms of inflammation as compared to the normal control group, suggesting UV-B radiation successfully induced inflammatory response in HRS/J hairless mice. Experimental groups 1 and 2 showed a significant reduction in inflammatory response when compared to the pathological control group. These data suggest that *Solanum incanum* L. solution and *Solanum incanum* L. gel have anti-inflammatory effects.

B. Analysis of Transepidermal Water Loss (TEWL)

Figure 2:
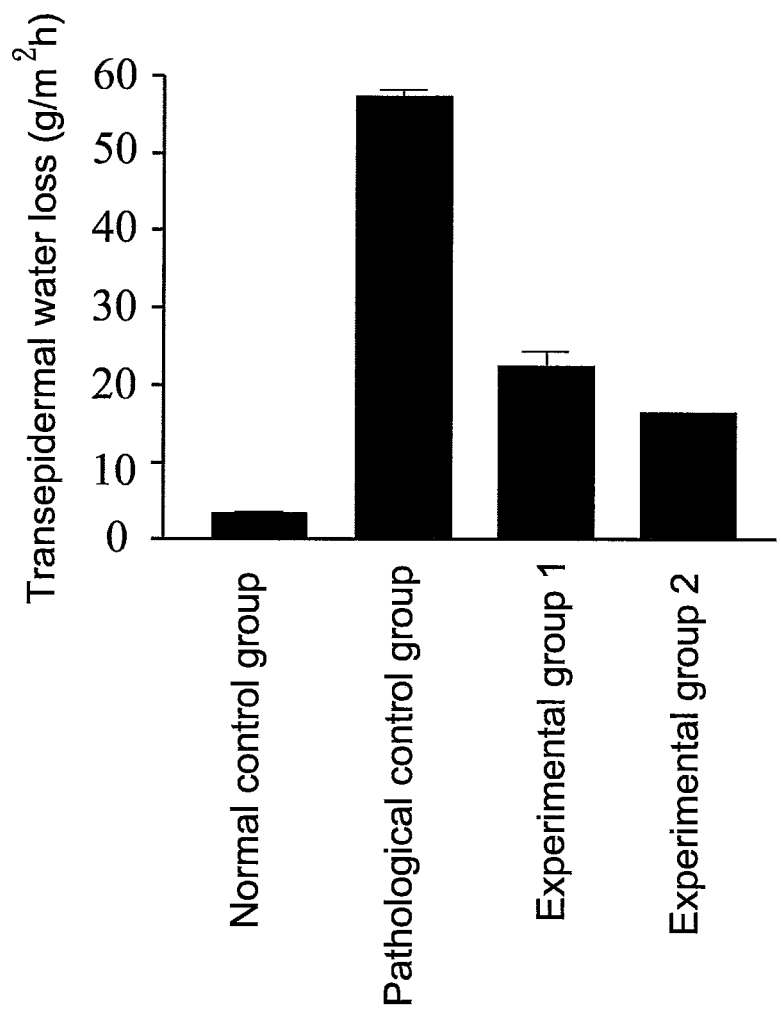
FIG. 2 shows transepidermal water loss (TEWL) of dorsal skin of HRS/J hairless mice in each of normal control group, pathological control group, and experimental groups 1 and 2 after 6 weeks of UV-B radiation. HRS/J hairless mice in normal control group did not receive any treatment including UV-B radiation and the water-soluble extract. HRS/J hairless mice in pathological control group were exposed to UV-B radiation and were not treated with the water-soluble extract. In experimental group 1, HRS/J hairless mice were exposed to UV-B radiation and were treated with *Solanum incanum* L. solution containing the water-soluble extract. In experimental group 2, HRS/J hairless mice were exposed to UV-B radiation and were treated with *Solanum incanum* L. gel containing the water-soluble extract.

FIG. 2 is a graph showing the results of TEWL of the dorsal skins of the HRS/J hairless mice in normal control group, pathological group and experimental groups 1 and 2. The HRS/J hairless mice from pathological group showed an increased level of TEWL as compared to the normal control group. This indicates that UV-B radiation induced TEWL in HRS/J hairless mice and damaged the barrier function of stratum corneum. HRS/J hairless mice from experimental groups 1 and 2 showed a marked decrease in TEWL when compared to pathological control group. In all, these data suggest that *Solanum incanum* L. solution and *Solanum incanum* L. gel can improve stratum corneum damage and inflammation caused by UV-B radiation.

C. Western Blot Analysis of NF-κB, COX-2 and iNOS

Figure 3:
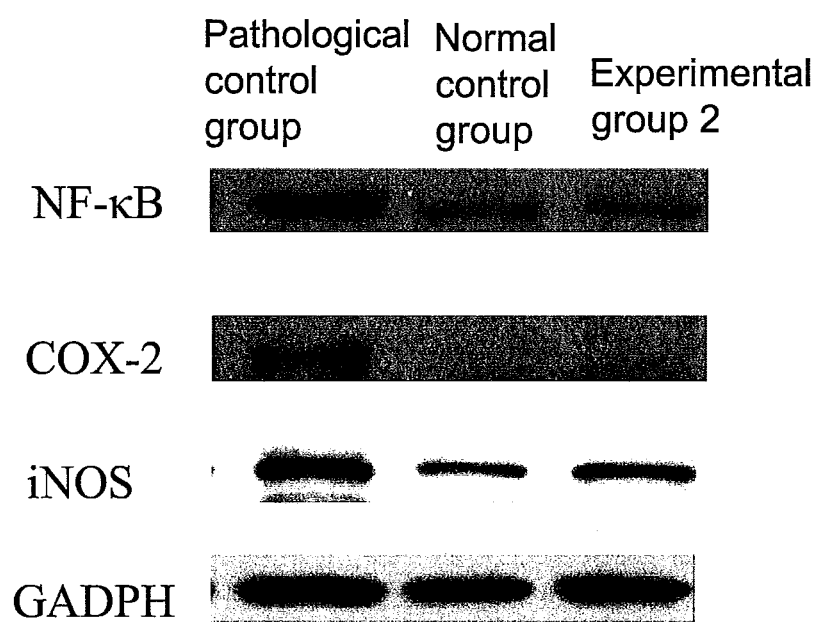
FIG. 3 is a western blot showing expressions of NF-kB, COX-2 and iNOS from dorsal skin tissue of HRS/J hairless mice after the 60 week experimental period. HRS/J hairless mice in normal control group did not receive any treatment including UV-B radiation and the water-soluble extract. HRS/J hairless mice in pathological control group were exposed to UV-B radiation and were not treated with the water-soluble extract. In experimental group 2, HRS/J hairless mice were exposed to UV-B radiation and were treated with *Solanum incanum* L. gel containing the water-soluble extract.

FIG. 3 is a western blot analysis of NF-κB, COX-2 and iNOS of dorsal skin tissue from HRS/J hairless mice in normal control group, pathological group and experimental group 2. The skin tissues from the pathological control group showed an increased expression of NF-κB, COX-2 and iNOS as compared to normal control group, suggesting that UV-B radiation induces inflammatory response in HRS/J hairless mice. A significant reduction of NF-κB, COX-2 and iNOS levels were observed in experimental group 2 when compared to pathological control group. In all, these data suggest that *Solanum incanum* L. gel have anti-inflammatory effects.

D. Immunohistochemistry Stain of NF-κB

Figure 4:
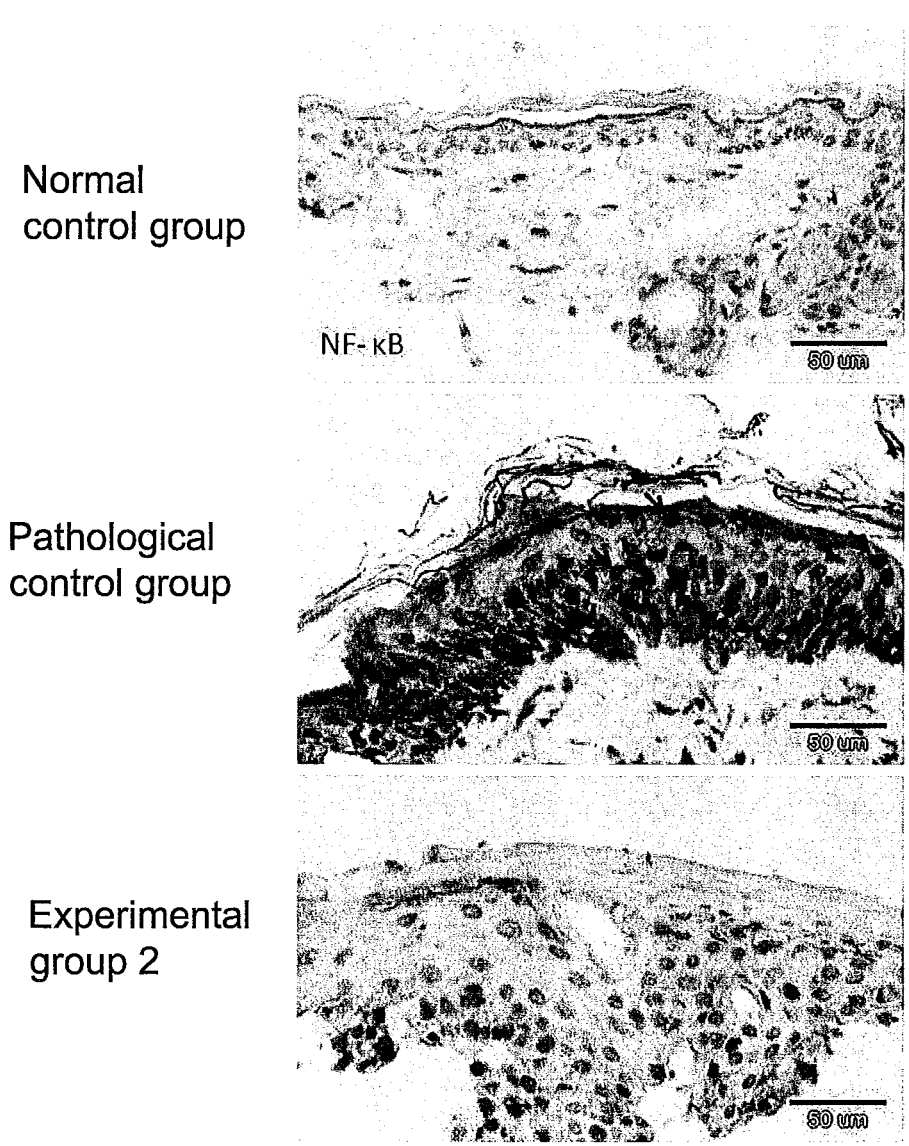
FIG. 4 shows an immunohistochemistry of NF-kB expression on dorsal skin tissue from HRS/J hairless mice at the end of 60 weeks after the first time of UV-B radiation. HRS/J hairless mice in normal control group did not receive any treatment including UV-B radiation and the water-soluble extract. HRS/J hairless mice in pathological control group were exposed to UV-B radiation and were not treated with the water-soluble extract. In experimental group 2, HRS/J hairless mice were exposed to UV-B radiation and were treated with *Solanum incanum* L. gel containing the water-soluble extract.

FIG. 4 shows an immunohistochemistry stain of NF-κB expression on dorsal skin tissue obtained from HRS/J hairless mice. As shown in FIG. 4, pathological control group showed an increased expression level in NF-κB as compared to the normal control group, suggesting UVB radiation induces inflammatory response in the HRS/J hairless mice. When *Solanum incanum* L. gel was applied to HRS/J hairless mice, as in experimental group 2, the expression of NF-κB showed a significant decrease when compared to the pathological control group. In all, these data suggest that *Solanum incanum* L. gel of the present invention has anti-inflammatory effect.

E. Histochemistry Stain of Mast Cells

Figure 5:
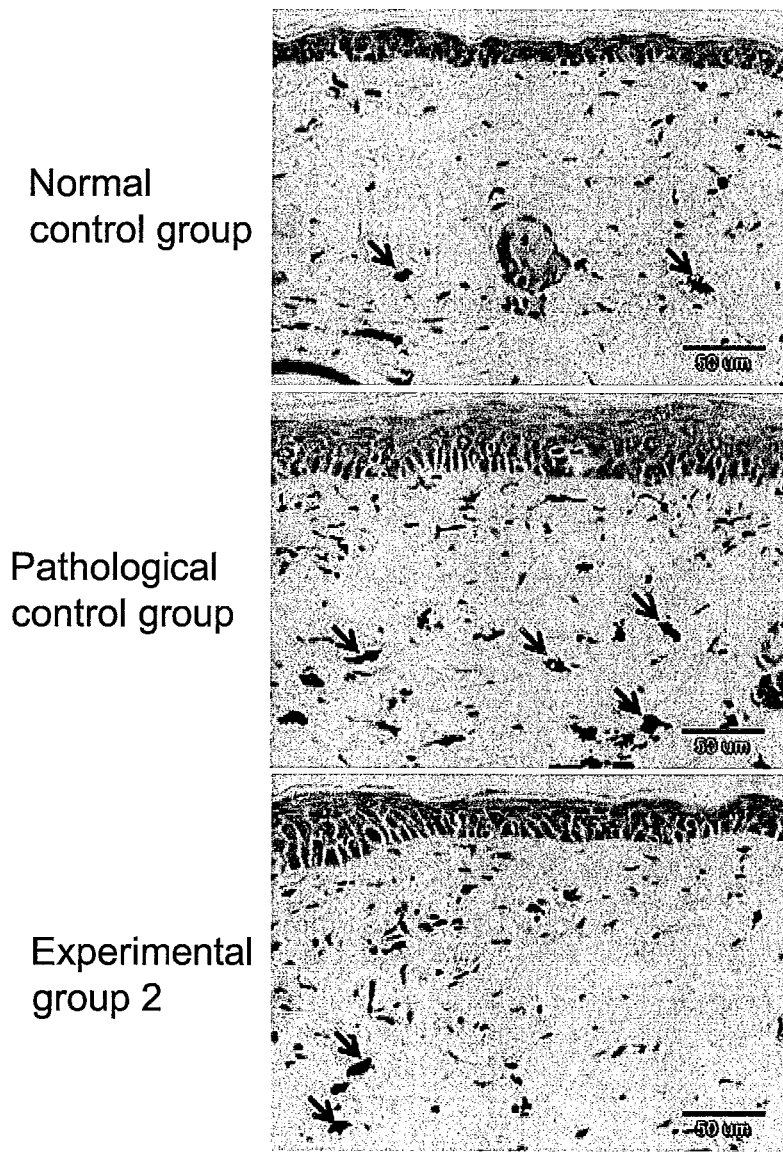
FIG. 5 shows a toluidine blue stain of dorsal skin tissue from HRS/J hairless mice at the end of the 60 week experimental period. HRS/J hairless mice in normal control group did not receive any treatment including UV-B radiation and the water-soluble extract. HRS/J hairless mice in pathological control group were exposed to UV-B radiation and were not treated with the water-soluble extract. In experimental group 2, HRS/J hairless mice were exposed to UV-B radiation and were treated with *Solanum incanum* L. gel containing the water-soluble extract. Arrows indicate the locations of infiltrated mast cells.

FIG. 5 shows a histochemistry stain of mast cells obtained from the dorsal skin tissue of HRS/J hairless mice. As shown in FIG. 5, toluidine blue staining revealed an extensive mast cell infiltration in dorsal skin tissue from the pathological control group. This phenomenon was not visibly clear in the normal control group. Apparently, mast cell infiltration was significantly reduced in experimental group 2 as compared to the pathological control group.

Figure 6:
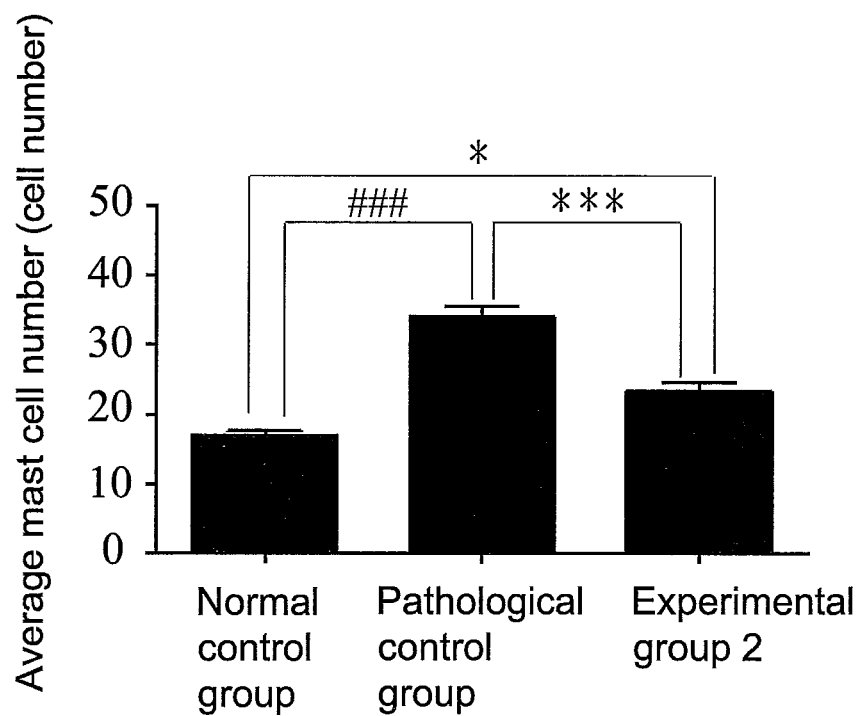
FIG. 6 is a bar diagram showing average mast cell number from dorsal skin tissue of HRS/J hairless mice in normal control group, pathological control group, and experimental group 2 after the 60 week experimental period. HRS/J hairless mice in normal control group did not receive any treatment including UV-B radiation and the water-soluble extract. HRS/J hairless mice in pathological control group were exposed to UVB radiation and were not treated with the water-soluble extract. In experimental group 2, HRS/J hairless mice were exposed to UV-B radiation and were treated with *Solanum incanum* L. gel containing the water-soluble extract. "*" indicates p<0.05 between experimental group 2 and normal control group. "***" indicates p<0.01 between experimental group 2 and pathological control group. "###" indicates p<0.001 between pathological control group and normal control group.

A comparison of mast cell number in each of normal control group, pathological group and experimental group 2 is shown in FIG. 6. Experimental group 2 showed a significant decrease of mast cell number when compared to pathological control group. These data suggest that *Solanum incanum* L. gel can improve the inflammatory effect induced by UVB radiation in HRS/J hairless mice.

Example 3

Evaluation of the Therapeutic Effects of the *Solanum incanum* L. Solution and the *Solanum incanum* L. Gel on Hairless Mice with UV-B-induced Photodamage Experimental Procedures:

HRS/J hairless mice was randomly grouped into normal control group, pathological control group and two experimental groups (i.e., experimental groups 1 and 2) (n=4/group). HRS/J hairless mice in normal control group did not receive any UV-B radiation treatment. Inflammation was induced in mice from pathological control group and two experimental groups as described in the section of "2. Induction of inflammation and photodamage" under "General Methods".

Starting from the initiation of UV-B radiation, HRS/J mice in experimental group 1 was administered orally with *Solanum incanum* L. solution, in which the solution was prepared as described in the section of "1. Preparations of water-soluble extract from *Solanum incanum* L. and *Solanum incanum* L. solution containing the water-soluble extract" under "Experimental Materials". These mice were administered with *Solanum incanum* L. solution once a day (1500 mg/kg), 7 times a week, during a 14-week period, and was continuously observed for 60 wks (i.e., 60 wk experimental period). In experimental group 2, the *Solanum incanum* L. gel prepared according to the section of "2. Preparation of *Solanum incanum* L. gel containing the water-soluble extract" under "Experimental Materials" was applied to dorsal skin of the mice subjected to UV-B radiation. The gel was applied once a day (dosage: 10-20 mg of gel per $cm^2$), 5 times a week, during a 14-wk period, and was observed for 60 wks. HRS/J hairless mice in normal control and pathological control group were not treated with the *Solanum incanum* L. solution or the *Solanum incanum* L. gel.

At the end of 26, 35, 38, 41, 52, 56, and 60 wks during the 60 wk experimental period, the dorsal skin from HRS/J hairless mice in pathological control and experimental groups 1 and 2 were subjected to analyses in Item A (see below). In addition, after the 60 wk experimental period, the dorsal skin obtained from HRS/J hairless mice in normal control, pathological control and experimental group 2 were subjected to analyses in Item B as described below. The dorsal skin tissues of the mice from pathological control and experimental group 2 were obtained using surgical scissors and were subjected to analyses in Item C as described below.

A. Analysis of Skin Tumor Formation

Tumor number on the dorsal skin of HRS/J hairless mice from pathological control and experimental groups 1 and 2 were observed by naked eyes. Tumor size was recorded using digital caliper (Mitutoyo, NTD15P-6"CX). Data for tumor number and volume are shown as mean±SEM ($p<0.05$ is statistically significant).

B. Evaluation of Skin Elasticity

Skin elasticity was evaluated by referencing pinch testing that is mentioned in K. Tsukahara et al (2005), *Biolo. Pharm. Bull.*, 28 (12):2302-2307. In brief, HRS/J hairless mice from normal control, pathological control and experimental group 2 were placed on a platform. The dorsal skin at the middle line of mouse body was pinched upward as much as possible (without lifting the mouse) and then released. The recovery time for the pinched skin to rebound to the original statue was measured.

C. Histochemical Staining of Elastic Fiber

After the 60 wk experimental period, the skin tissues obtained from HRS/J hairless mice in pathological control and experimental group 2 were sectioned into 6 μm thickness using the procedure set forth in the section of "3. Tissue slice" under "General Methods". Tissue sections were stained with resorcin-fuchsin solution, Weigert's iron hematoxylin and van Gieson's solution (all purchased from Muto Pure Chemicals Co., Ltd). Stained tissues were observed under an optical microscope with a 100-400× magnification and recorded with a digital camera (Olympus DP50, Japan).

Results:

A. Analysis of Skin Tumor Formation

Figure 7:
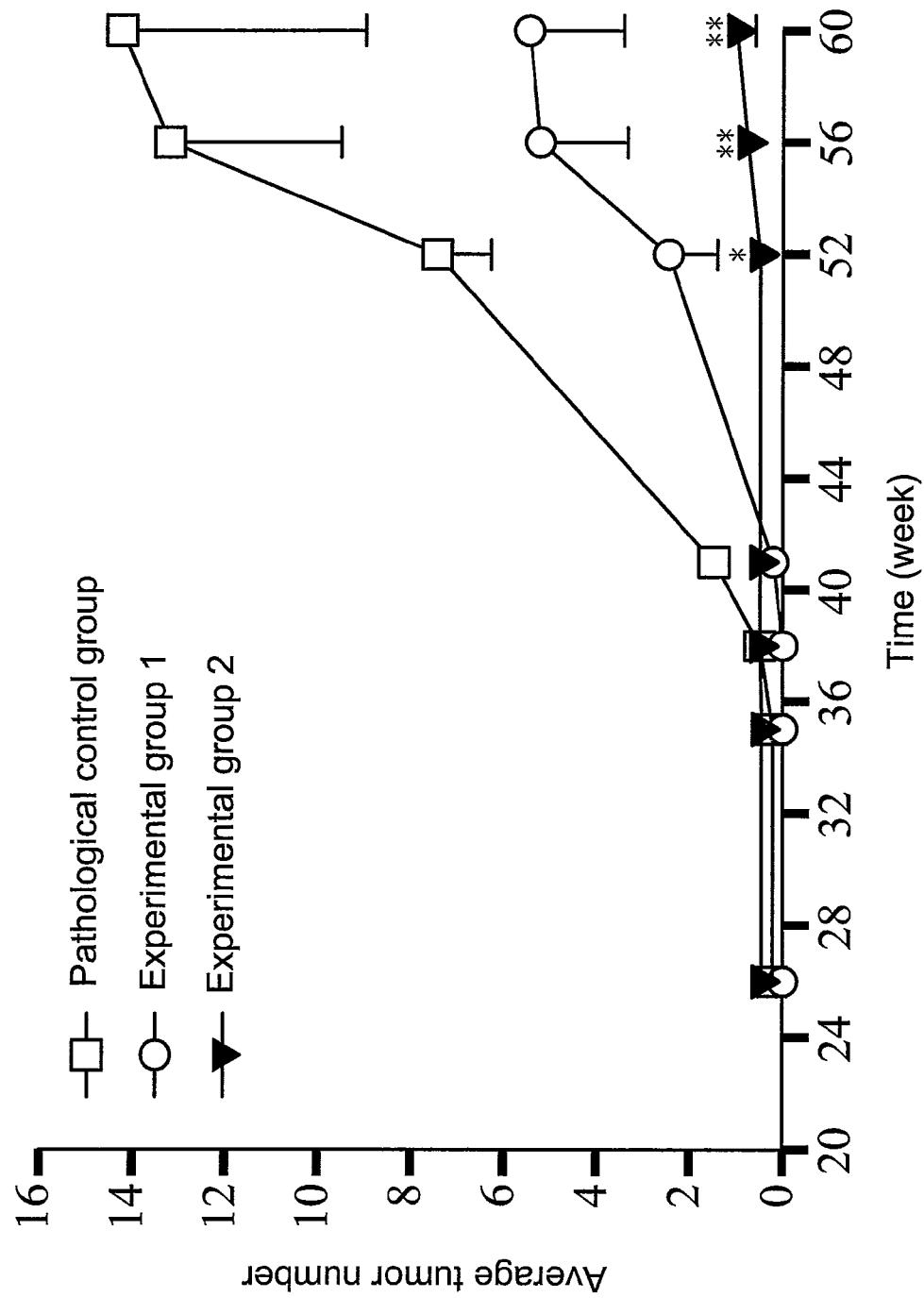
FIG. 7 is a plot showing average tumor number in HRS/J mice formed at various time points during the 60 week experimental period. HRS/J hairless mice in pathological control group had photodamage induced by UV-B radiation and were not treated with the water-soluble extract. HRS/J hairless mice in experimental group 1 were exposed to UV-B radiation and were treated with *Solanum incanum* L. solution containing the water-soluble extract. In experimental group 2, HRS/J hairless mice were exposed to UV-B radiation and were treated with *Solanum incanum* L. gel containing the water-soluble extract. "*" indicates p<0.05 between experimental group 2 and pathological control group. "*" indicates p<0.01 between experimental group 2 and pathological control group.

Tumor number over the course of the 60 wk experimental period is shown in FIG. 7. Tumor size measurement over the course of the 60 wk experimental period is shown in FIG. 8.

Figure 8:
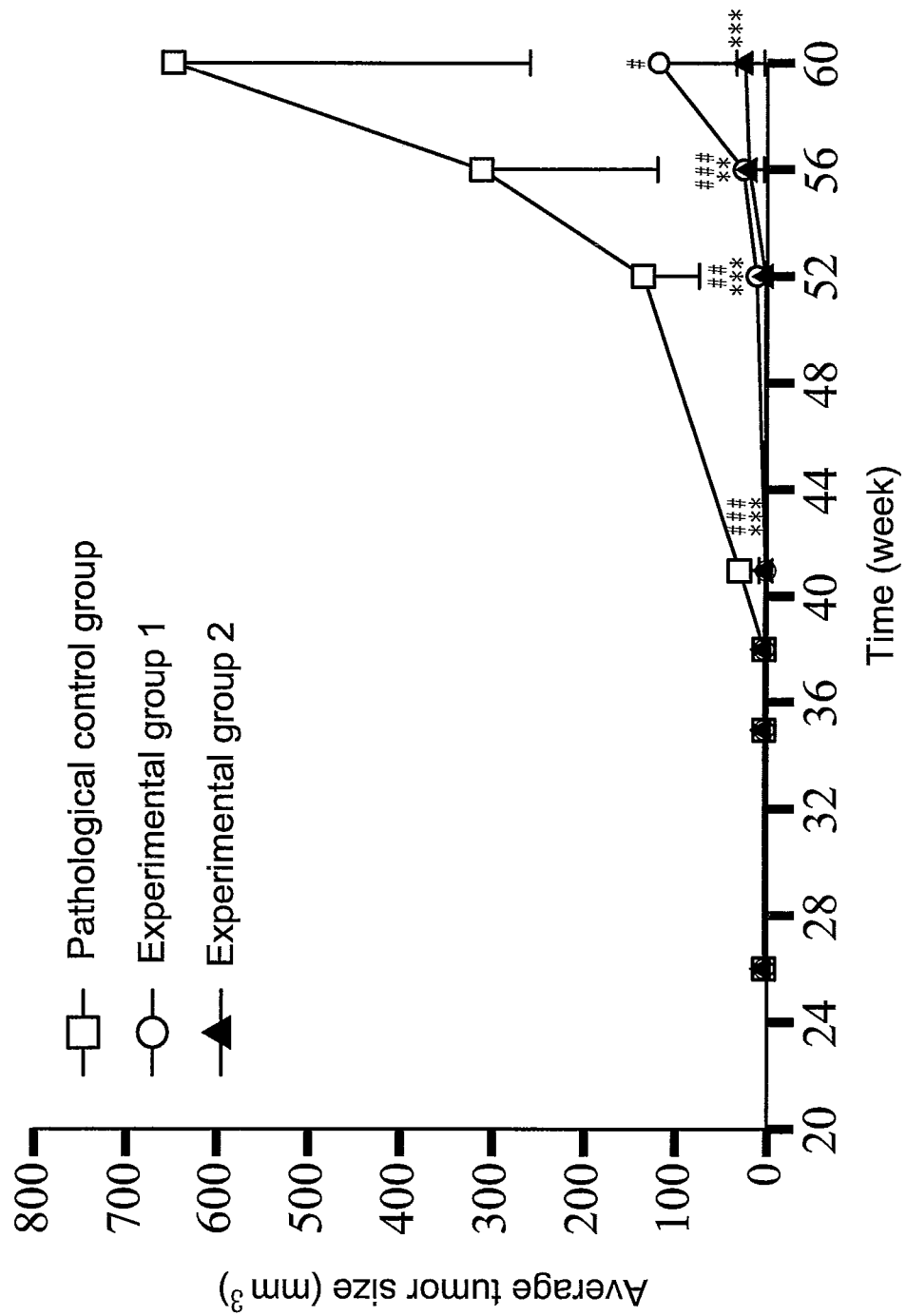
FIG. 8 is a plot showing average tumor size in HRS/J hairless mice at various time points during the 60 week experimental period. HRS/J hairless mice in pathological control group had photodamage induced by UV-B radiation and were not treated with the water-soluble extract. HRS/J hairless mice in experimental group 1 were exposed to UV-B radiation and were treated with *Solanum incanum* L. solution containing the water-soluble extract. HRS/J hairless mice in experimental group 2 were exposed to UV-B radiation and were treated with *Solanum incanum* L. gel containing the water-soluble extract. "#" indicates p<0.05 between experimental group 1 and pathological control group. "##" indicates p<0.01 between experimental group 1 and pathological control group. "###" indicates p<0.001 between experimental group 1 and pathological control group. "" indicates p<0.01 between experimental group 2 and pathological control group. "*" indicates p<0.001 between experimental group 2 and pathological control group.

As shown in FIGS. 7 and 8, at 38 wk, the dorsal skin of the HSR/J hairless mice from the pathological control group showed an acceleration of tumor development. Conversely, a slower increase in tumor number and size was observed in experimental groups 1 and 2 during the 60 wk experimental period. These data suggest that *Solanum incanum* L. solution and *Solanum incanum* L. gel can improve the photodamage caused by UV-B radiation and alleviate skin pathologic change caused by photodamage.

B. Evaluation of Skin Elasticity

Figure 9:
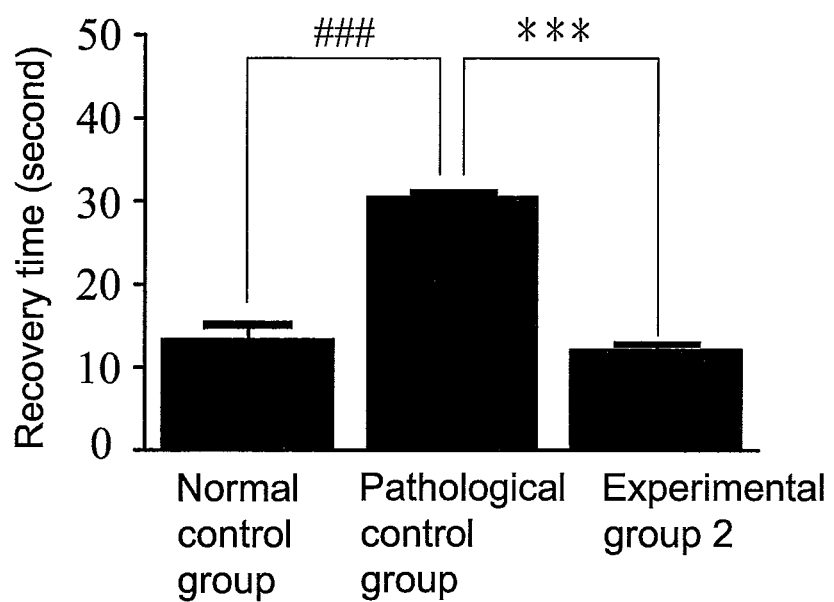
FIG. 9 is a bar diagram showing recovery time in pinch test on HRS/J hairless mice after the 60 week experimental period. HRS/J hairless mice in normal control group did not receive any treatment including UV-B radiation and the water-soluble extract. HRS/J hairless mice in pathological control group were exposed to UV-B radiation and were not treated with the water-soluble extract. In experimental group 2, HRS/J hairless mice were exposed to UV-B radiation and were treated with *Solanum incanum* L. gel containing the water-soluble extract. "*" indicates p<0.001 between experimental group 2 and pathological control group. "###" indicates p<0.001 between pathological control group and normal control group.

Pinch testing was done after the 60 wk experimental period on HRS/J hairless mice from normal control, pathological control and experimental group 2. As shown in FIG. 9, pathological control group showed a decreased elasticity compared to the normal control group since a longer recovery time is required in the pathological control group; suggesting UV-B exposure induces photodamage in HRS/J hairless mice. When *Solanum incanum* L. gel was applied to dorsal skin of hairless mice in experimental group 2, skin elasticity was greatly increased when compared to the pathological control group. Data from these experiments suggest that *Solanum incanum* L. gel can alleviate photodamage caused by UV-B and improve skin elasticity.

C. Histochemical Staining of Elastic Fiber

Figure 10:
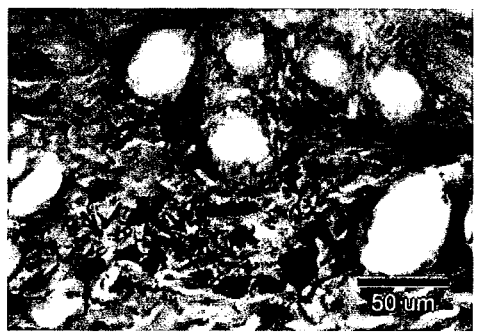
FIG. 10 shows images of elastic fibers of dorsal skin tissue stained with resorcin-fuchsin solution, Weigert's iron hematoxylin and van Gieson solution. HRS/J hairless mice in pathological control group had photodamage induced by UV-B radiation and were not treated with the water-soluble extract. In experimental group 2, HRS/J hairless mice were exposed to UV-B radiation and were treated with *Solanum incanum* L. gel containing the water-soluble extract. Arrows indicate the locations of elastic fiber denaturation.
Figure 10:
Figure 10:
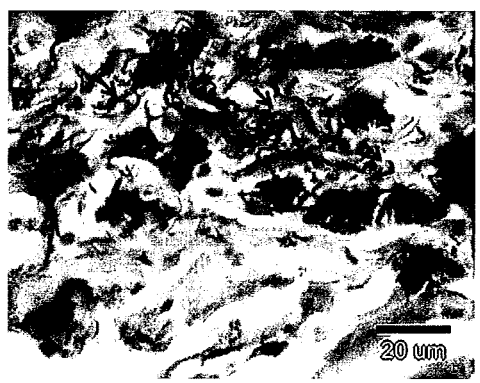
Figure 10:
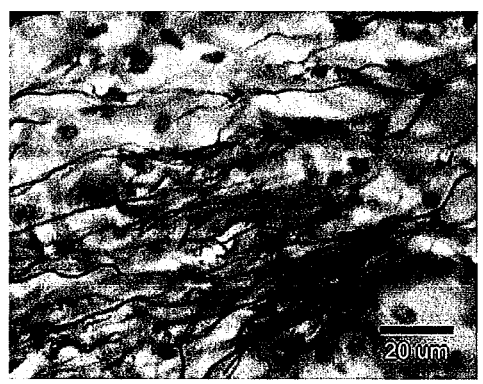

As shown in FIG. 10, the occurrence of elastic fiber denaturation was markedly increased in pathological control group. On the other hand, when *Solanum incanum* L. gel was applied to the dorsal skin of hairless mice in experimental group 2, there was less occurrence of elastic fiber denaturation and the fibers remained long and intact. Data from these experiments suggest that *Solanum incanum* L. gel of the present invention can alleviate photodamage caused by UV-B exposure and improve solar elastosis.

In all, data from the above experiments support that the water-soluble extract from *Solanum incanum* L. can prevent photodamage and improve pathological changes on the skin caused by photodamage.

Example 4

Comparison of the Effect of the *Solanum incanum* L. Gel and Tretinoin on Preventing Uv-B-induced Photodamage Experimental Procedures:

HRS/J hairless mice was randomly grouped into pathological control group, tretinoin group and *Solanum incanum* L. gel group (n=5/group). Induction of photodamage on HRS/J hairless mice from each group was performed according to the section of "2. Induction of inflammation and photodamage" under "General Methods".

Starting from the initiation of UV-B radiation, HRS/J mice in tretinoin group was applied with AIROL vanishing cream (contains 0.05% tretinoin, a conventional active component for treating photodamage, topical dosage: 10 to 20 mg of AIROL vanishing cream per $cm^2$). The cream was applied once a day, 5 times a week, for 14 weeks, and was continuously observed for 35 weeks (i.e., 35 week experimental period). The dorsal skin of HRS/J hairless mice in *Solanum incanum* L. gel group was applied with the *Solanum incanum* L. gel obtained from the section of "2. Preparation of *Solanum incanum* L. gel containing the water-soluble extract" under "Experimental Materials". The gel was applied once a day (dosage: 10-20 mg of gel/$cm^2$), 5 times a week, during a 14-week period and was observed for 35 weeks. HRS/J hairless mice in pathological control group were not treated with the water-soluble extract.

Tumor number on the dorsal skin of the mice from tretinoin group and *Solanum incanum* L. gel group was quantified at 0 week (i.e., before exposure to UV-B radiation), and at the end of 2, 7, 12, 17, 22, 27, and 32 weeks during the 35 week experimental period based on the method mentioned in Item A (Analysis of skin tumor formation) of Example 3. In addition, HRS/J hairless mice from pathological control, tretinoin group, and *Solanum incanum* L. gel group were subjected to analyses as mentioned in Item B (Analysis of transepidermal water loss) of Example 2 and the following Item A at 0 week and the end of 5, 10, 15, 20, 25, and 30 weeks during the 35 week experimental period.

A. Examination of Water Content in Skin

Determination of water content in skin was examined by using an evaporimeter (Tewameter TM 201R, Courage & Khazaka, Cologne, Germany).

(1) Analysis of Skin Tumor Formation

Figure 11:
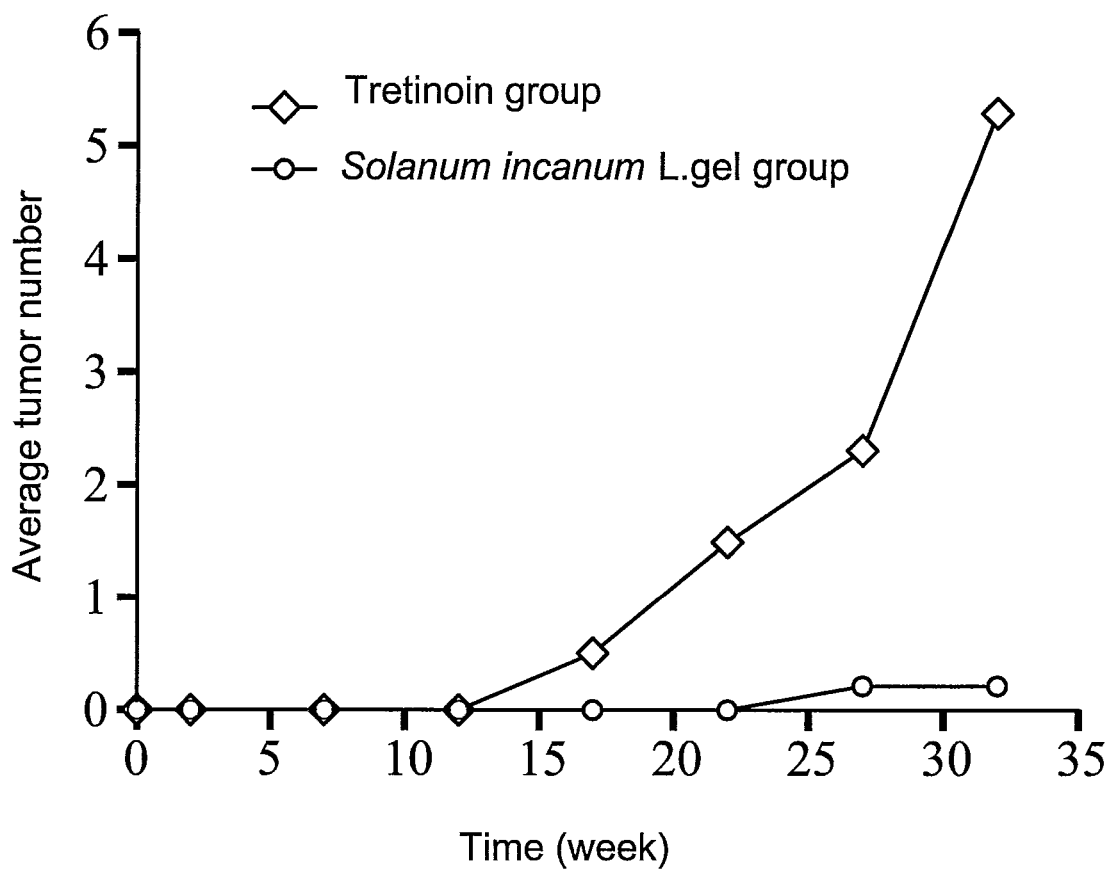
FIG. 11 shows average tumor number in HRS/J hairless mice over the experimental period. HRS/J hairless mice were exposed to UV-B radiation and were treated with AIROL vanishing cream in tretinoin group. In *Solanum incanum* L. gel group, HRS/J hairless mice were exposed to UV-B radiation and were treated with *Solanum incanum* L. gel containing the water-soluble extract.

As shown in FIG. 11, at week 17, tretinoin group showed a dramatic increase in average tumor number. Conversely, HRS/J hairless mice from *Solanum incanum* L. gel group showed a slow increase in average tumor number. These data suggest that *Solanum incanum* L. gel of the present invention can more effectively improve photodamage caused by UV-B when compared to tretinoin group, and alleviates pathological changes of the skin.

(2) Evaluation of Transdermal Water Loss (TEWL)

Figure 12:
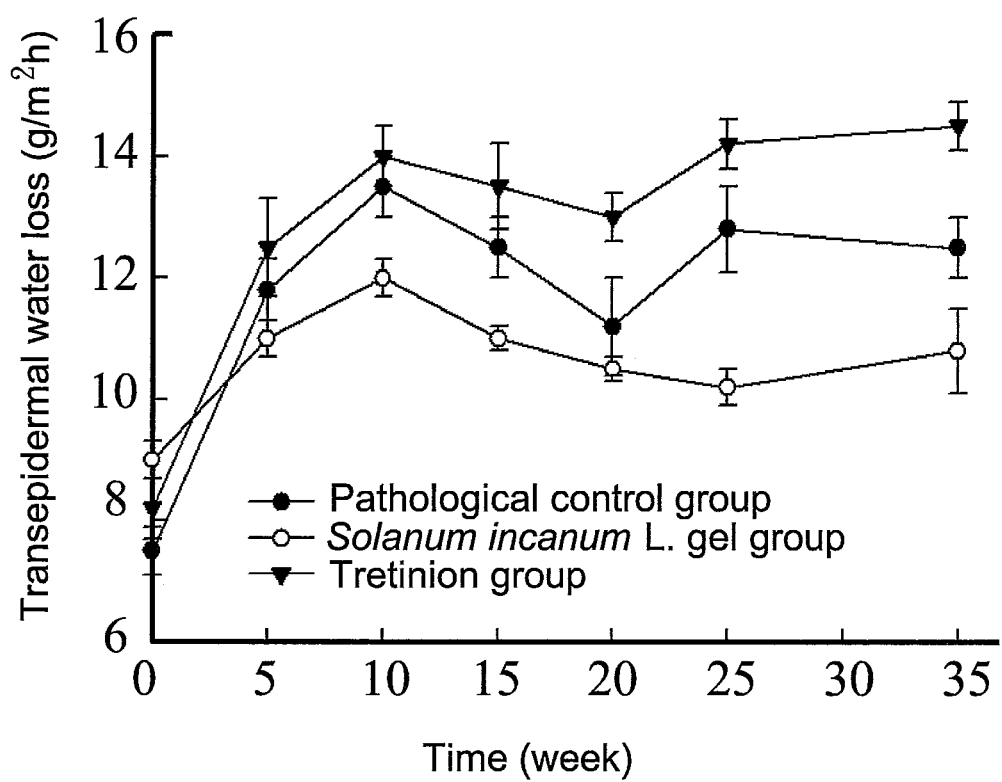
FIG. 12 is a graph showing transepidermal water loss (TEWL) over the experimental period. HRS/J hairless mice in pathological control group were exposed to UV-B radiation and were not treated with the water-soluble extract. HRS/J hairless mice in tretinoin group were exposed to UV-B radiation and were treated with AIROL vanishing cream. In *Solanum incanum* L. gel group, HRS/J hairless mice were exposed to UV-B radiation and were treated with *Solanum incanum* L. gel containing the water-soluble extract. "*" indicates p<0.05 between tretinoin group and *Solanum incanum* L. gel group.

As shown in FIG. 12, during the 35 week experimental period, TEWL rate was lower in *Solanum incanum* L. gel group when compared to pathological and tretinoin groups. Specifically, at the end of 20, 25 and 30 weeks during the 35 week experimental period, there was a statistically significant difference in TEWL between the pathological control group and *Solanum incanum* L. gel group ($p<0.05$). These data suggest that *Solanum incanum* L. gel of the present invention can effectively alleviate photodamage induced by UV-B radiation and improve damage on stratum corneum caused by photodamage.

(3) Evaluation of Water Content in Skin

Figure 13:
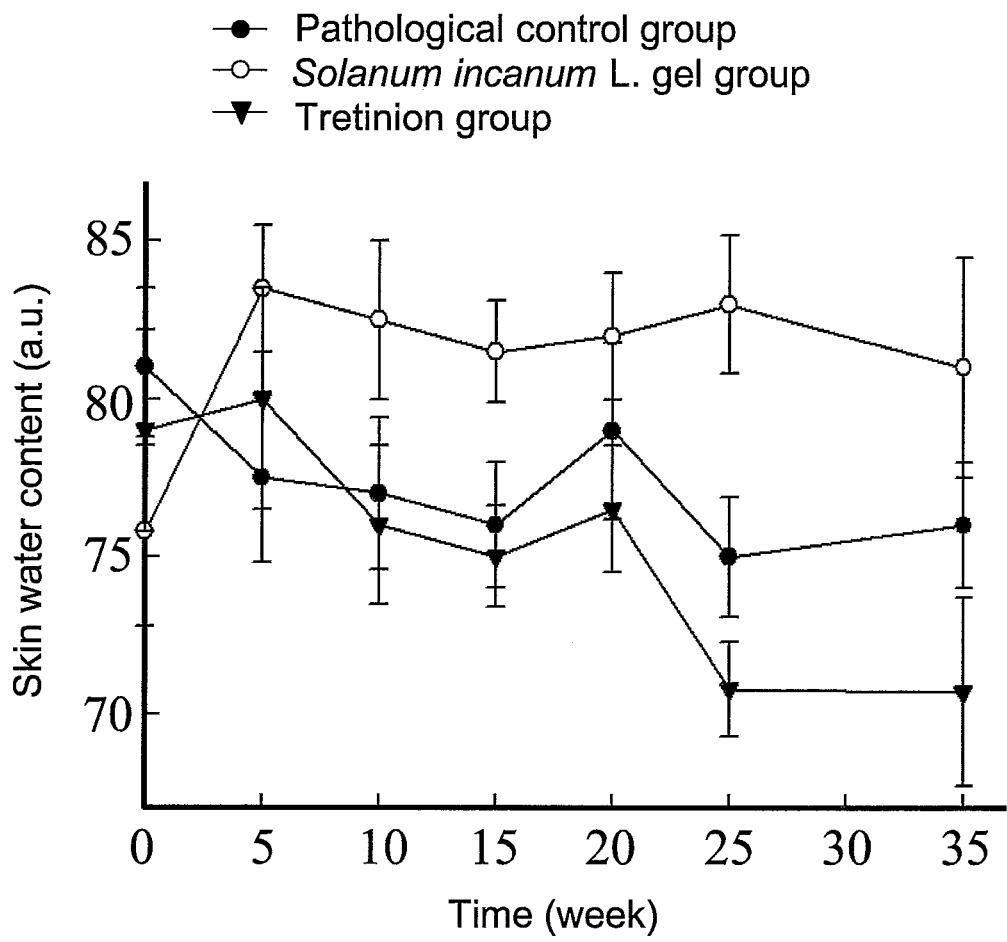
FIG. 13 is a graph showing water content of dorsal skin from HRS/J hairless mice over the experimental period. HRS/J hairless mice in pathological control group had photodamage induced by UV-B radiation and were not treated with the water-soluble extract. In tretinoin group, HRS/J hairless mice were exposed to UV-B radiation and were treated with AIROL vanishing cream. In *Solanum incanum* L. gel group, HRS/J hairless mice were exposed to UV-B radiation and were treated with *Solanum incanum* L. gel containing the water-soluble extract. "*" indicates p<0.05 between tretinoin group and *Solanum incanum* L. gel group.

Water content in the dorsal skin of HRS/J hairless mice from each group (pathological control, tretinion and *Solanum incanum* L. gel groups) was determined at various time points throughout the 35 week experimental period. As shown in FIG. 13, the mice treated with *Solanum incanum* L. gel had a higher skin water content when compared to pathological control group and tretinoin group. Specifically, at the end of 25 weeks, the mice treated with *Solanum incanum* L. gel showed a statistically significant water content as compared to the pathological group or tretinoin group. These data suggest that *Solanum incanum* L. gel of this invention is more effective in alleviating photodamage caused by UV-B and improve skin water loss than tretinion treatment.

In all, the water-soluble extract of this invention has been proven to exhibit prevention of photodamage, improvement of pathological changes caused by photodamage, and maintenance of moisture-retaining capacity more effectively than what is often clinically used to treat and prevent photodamage (such as tretinion).

All the patents and literature references cited in the present specification as well as the references described therein, are hereby incorporated by reference in their entirety. In case of conflict, the present description, including definitions, will prevail.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A method for treating a cutaneous photodamage, comprising applying to a subject in need of such treatment a water-soluble extract from a plant of *Solanum* genus, the water-soluble extract comprising solamargine and solasonine, wherein at least one symptom of the cutaneous photodamage is alleviated.

2. The method of claim 1, wherein the water-soluble extract comprises at least 60 wt % of solamargine and solasonine.

3. The method of claim 1, wherein the water-soluble extract comprises 60 wt %-90 wt % of solamargine and solasonine.

4. The method of claim 1, wherein the cutaneous photodamage comprises one of the following symptoms:
thinning of the skin, skin atrophy, decrease in collagen fiber and elastic fiber, elastosis, loss of skin elasticity, dryness, wrinkle formation, inflammatory cells infiltration, premature skin aging, vascular change, pigmentary change, comedone, and cyst.

5. The method of claim 1, wherein the water-soluble extract is applied in an oral dosage form.

6. The method of claim 1, wherein the water-soluble extract is applied in a topical dosage form.

7. A method for alleviating a skin of a subject from a photodamage, comprising applying to the skin of the subject in need of such alleviation a cosmetic composition that contains a water-soluble extract from a plant of *Solanum* genus, the water-soluble extract comprising solamargine and solasonine, wherein at least one symptom of the photodamage is alleviated.

8. The method of claim 7, wherein the water-soluble extract comprises at least 60 wt % of solamargine and solasonine.

9. The method of claim 7, wherein the water-soluble extract comprises 60 wt %-90 wt % of solamargine and solasonine.

10. The method of claim 7, further comprising a cosmetically acceptable adjuvant selected from the group consisting of solvent, gelling agents, activating agents, preservatives, antioxidants, screening agents, chelating agents, surfactants, coloring agents, thickening agents, fillers, fragrance and odor absorbent.

11. A method for treating an inflammation, comprising:
applying to a subject in need of such treatment, a water-soluble extract from a plant of *Solanum* genus, the water-soluble extract comprising solamargine and solasonine, wherein the inflammation is reduced.

12. The method of claim 11, wherein the water-soluble extract comprises at least 60 wt % of solamargine and solasonine.

13. The method of claim 11, wherein the water-soluble extract comprises 60 wt %-90 wt % of solamargine and solasonine.

14. The method of claim 11, wherein the water-soluble extract is applied in an oral dosage form.

15. The method of claim 11, wherein the water-soluble extract is applied in a topical dosage form.

* * * * *